(12) United States Patent
Stamler

(10) Patent No.: US 11,559,498 B2
(45) Date of Patent: Jan. 24, 2023

(54) COMPOSITIONS AND METHODS FOR IN VIVO LUNG AND BLOOD SNO REPLETION

(71) Applicant: UNIVERSITY HOSPITALS CLEVELAND MEDICAL CENTER, Cleveland, OH (US)

(72) Inventor: Jonathan S. Stamler, Shaker Heights, OH (US)

(73) Assignee: UNIVERSITY HOSPITALS CLEVELAND MEDICAL CENTER, Cleveland, OH (US)

(*) Notice: Subject to any disclaimer, the term of this patent is extended or adjusted under 35 U.S.C. 154(b) by 0 days.

(21) Appl. No.: 17/562,087

(22) Filed: Dec. 27, 2021

(65) Prior Publication Data
US 2022/0117909 A1   Apr. 21, 2022

Related U.S. Application Data

(60) Provisional application No. 63/014,585, filed on Apr. 23, 2020.

(51) Int. Cl.
| | |
|---|---|
| *A61K 31/04* | (2006.01) |
| *A61P 11/00* | (2006.01) |
| *A61K 9/00* | (2006.01) |
| *A61K 31/198* | (2006.01) |

(52) U.S. Cl.
CPC ............. *A61K 31/04* (2013.01); *A61K 9/0073* (2013.01); *A61K 31/198* (2013.01); *A61P 11/00* (2018.01)

(58) Field of Classification Search
CPC ...................................................... A61K 31/04
See application file for complete search history.

(56) References Cited

U.S. PATENT DOCUMENTS

2001/0012834 A1* 8/2001 Stamler .................. A61P 29/00
                                                                514/474
2013/0178499 A1    7/2013 Sun et al.

FOREIGN PATENT DOCUMENTS

WO    2007146311      * 12/2007
WO    2007146311 A2    12/2007

OTHER PUBLICATIONS

Reilly et al., Am J Physiol Lung Cell Mol Physiol, 2015, 308(1): L76-85.*
Barnett et al., Crit Rev Biochem Mol Biol, 2017, 52(3): 340-354.*
Raffay et al., Mol Pharmacol, 2016, 90(4): 418-26.*
Wikipedia, "COVID-19", Mar. 17, 2020, retrieved on May 7, 2021 from https://en.wikipedia.org/w/index.php?title=COVID-19&oldid=946010373; entire document, especially p. 1 para 1, p. 3 para 7.
Applicant: University Hospitals—Cleveland Medical Center; Title: "Compositions and Methods for in Vivo Lung and Blood SNO Repletion"; International PCT Application No. PCT/US21/28884 Filed: Apr. 23, 2021; PCT International Search Report and Written Opinion; Authorized Officer: Kari Rodriquez; 9 pg.

* cited by examiner

*Primary Examiner* — Rei Tsang Shiao
(74) *Attorney, Agent, or Firm* — Tarolli, Sundheim, Covell & Tummino LLP

(57) ABSTRACT

A method of treating coronavirus infection, post-acute sequelae of coronavirus infection, and viral mediated respiratory distress in a subject in need thereof includes administering to the subject a therapeutically effective amount of agent that promotes, increases, and/or induces hemoglobin nitrosylation within red blood cells (RBCs) and GSNO levels in the lung or airways of the subject.

19 Claims, 11 Drawing Sheets

Human Kidneys

B SNO-Treated

C

COMPOSITIONS AND METHODS FOR IN VIVO LUNG AND BLOOD SNO REPLETION

RELATED APPLICATION

This application claims priority from U.S. Provisional Application No. 63/014,585, filed Apr. 23, 2020, the subject matter of which is incorporated herein by reference in its entirety.

BACKGROUND

There is a need for the development of new treatments that are effective against respiratory stress associated with viral infections, particularly against viral infections, which are associated with high morbidity and mortality, and which impact on sizable populations. Treatments currently available are inadequate or ineffective in large proportions of infected patients.

For example, a well-known family of pathogenic viruses are the Coronaviruses. Coronaviruses (Order Nidovirales, family Coronaviridae, Genus Coronavirus) are enveloped positive-stranded RNA viruses that bud from the endoplasmic reticulum-Golgi intermediate compartment or the cis-Golgi network.

Coronaviruses infect humans and animals and it is thought that there could be a coronavirus that infects every animal. Two human coronaviruses, 229E and OC43, are known to be the major causes of the respiratory distress and can cause pneumonia in older adults, neonates, or immunocompromised patients. Animal coronaviruses can cause respiratory, gastrointestinal, neurological, or hepatic diseases in their host. Several animal coronavirus are significant veterinary pathogens.

Severe acute respiratory syndrome (SARS) is a viral respiratory disease caused by a SARS-associated coronavirus, such as SARS-CoV, MERS-CoV, and SARS-CoV-2. SARS is a respiratory illness that has been reported in Asia, North America, and Europe. It is believed that SARS-CoV infections will not be eradicated but will cause seasonal epidemics like the cold or influenza viruses. There is an ongoing need to identify therapeutics and/or treatments capable of treating respiratory distress mediated by viral infections.

SARS-CoV-2 is the pathogen responsible for coronavirus disease 2019 (COVID-19). COVID-19 is now recognized as a multi-organ disease with a broad spectrum of manifestations including microvascular thrombosis (impaired microvascular blood flow). Microvascular thrombosis associated with COVID-19 can cause widespread tissue injury and produce a newly encountered clinical syndrome of virally induced lung injury, lung inflammation and tissue hypoxia throughout the body from microvascular blood flow deficits.

Similar to post-acute viral syndromes described in survivors for other virulent coronavirus epidemics, there are increasing reports of persistent and prolonged effects after acute COVID-19. Post-acute COVID or post-acute sequelae of SARS-CoV-2 infection (PASC) is a syndrome characterized by persistent symptoms and/or delayed long-term complications beyond four weeks from the onset of acute symptoms. Symptoms of PASC can include fatigue, dyspnea, chest pain, cognitive disturbances, arthralgia, and decline in quality of life.

SUMMARY

Embodiments described herein relate to compositions and methods for in vivo blood and lung SNO repletion and to their use in treating coronavirus infection, such as severe acute respiratory coronavirus 2 (SARS-CoV-2) infection, coronavirus disease, such as COVID-19, and post-acute COVID or post-acute sequelae of SARS-CoV-2 infection (PASC). The compositions and methods described herein can also be used in methods of treating viral mediated respiratory distress associated with coronavirus infection.

In some embodiments, the methods can include administering to a subject having a coronavirus infection or COVID-19 a therapeutically effective amount of an agent that promotes, increases, and/or induces hemoglobin nitrosylation within red blood cells (RBCs) and GSNO levels in the lungs or airways of the subject. The administration of an agent that promotes, increases, and/or induces hemoglobin nitrosylation within red blood cells (RBCs) and GSNO levels in the lungs or airways of the subject can reduce and/or attenuate at least one component of, and preferentially the whole novel syndrome comprised of viral injury, inflammation, peripheral tissue hypoxemia/hemodynamic instability, microvascular blood flow disorder or an SNO-hemoglobin deficiency like state, associated with and/or caused by the coronavirus infection.

Respiratory distress mediated by viral injury, such as coronavirus injury to the pulmonary parenchyma, can include shunting and V/Q mismatch resulting in hypoxemia. Administration of an agent, which is able to increase SNOs in both airways and blood, such as SNO-generating compound ethyl nitrite (ENO), to subjects with viral associated respiratory distress by, for example, inhalation (unlike inhaled NO) can increase tissue oxygenation in a setting of reduced oxygen availability. Further, SNO generating compounds can prevent lung injury and inflammation in animal models, and SNOs, such as those generated by ENO administration, have significant anti-viral activity against various coronaviruses.

Moreover, a main form of NO bioactivity in the lungs is GSNO that is maintained enzymatically. GSNO is a potent S-nitrosylating agent that is endowed with bronchodilator, anti-inflammatory, anti-apoptotic, anti-microbial and antiviral activity. GSNO is thus a major component of the innate immune response. GSNO is also important for immune cell function and levels appear to decline in airway disease. Endogenous SNOs, and S-nitrosylation more generally, have been found to inhibit coronavirus infection, suggesting pan viral activity. This supports the use of SNO generating compounds to improve physiologic status in settings of reduced oxygen availability and lung injury. Notably, administration of a SNO generating compound, such as ENO, repletes GSNO levels in airways, as well as SNO-hemoglobin in blood (SNO-Hb, the main regulator of oxygen delivery in the microvasculature via blood flow), which shows clinical utility in treating coronavirus infections, such as SARS-CoV-2 infection, the related lung injury, and deficits in systemic oxygenation.

Furthermore, COVID-19 has been shown to cause widespread microvascular blood flow occlusion. Symptoms of PASC, such as such as fatigue, dyspnea, chest pain, chronic malaise, diffuse myalgia, depressive symptoms and non-restorative sleep, arthralgia, migraine-like headaches, cognitive impairment, including brain fog, which may manifest as difficulties with concentration, memory, receptive language and/or executive function, can be attributed to and/or associated with microvascular blood flow occlusion. Small blood vessel flow is controlled by SNO-Hb in RBCs and SNO donor or generating agents can be effective in repleting and enhancing SNO-Hb and microvascular blood flow in situ without excessively oxidizing hemoglobin or disrupting its allosteric regulation by oxygen.

Therefore, in some embodiments an agent that promotes, increases, and/or induces hemoglobin nitrosylation and GSNO levels in the lung or airways of a subject can be administered to a subject with respiratory distress mediated by viral injury, coronavirus infection, and/or PASC to restore SNO-regulated control over oxygen exchange and delivery, airway/vascular tone, peripheral tissue oxygenation and blood flow, as well as treat lung inflammation and lung injury and improve host defense.

In some embodiments, the agent is a SNO generating compound that increases hemoglobin nitrosylation within RBCs and GSNO levels in the lungs of the subject. The SNO generating compound can be in a gaseous form that does not directly release NO. The SNO generating compound in gaseous form can be administered by inhalation, ventilation, or insufflation.

In other embodiments, the SNO generating compound is ENO. ENO uniquely generates SNOs in lungs and blood to treat coronavirus infection, such as severe acute respiratory coronavirus 2 (SARS-CoV-2) infection, coronavirus disease, such as COVID-19, and post-acute COVID or post-acute sequelae of SARS-CoV-2 infection (PASC). ENO can be administered in a composition at a concentration of 0.1 to 5,000 ppm, preferably 0.1 to 2,000 ppm, more preferably 0.1 to 2,000 ppm, even more preferably 1 to 1000 ppm.

In other embodiments, an agent that promotes, increases, and/or induces hemoglobin nitrosylation within RBCs and GSNO levels in the lung or airways of the subject can be a GSNO reductase (GSNOR) inhibiting agent. The GSNOR inhibiting agent can be selected from an ADH inhibitor, an AKR inhibitor and/or a SNO-CoAR inhibitor. The GSNOR inhibiting agent can be administered to the subject via parenteral or enteral administration at an amount effective to increase the level of hemoglobin nitrosylation within RBCs and GSNO in the subject's lung tissue.

DETAILED DESCRIPTION

Figure 1A:
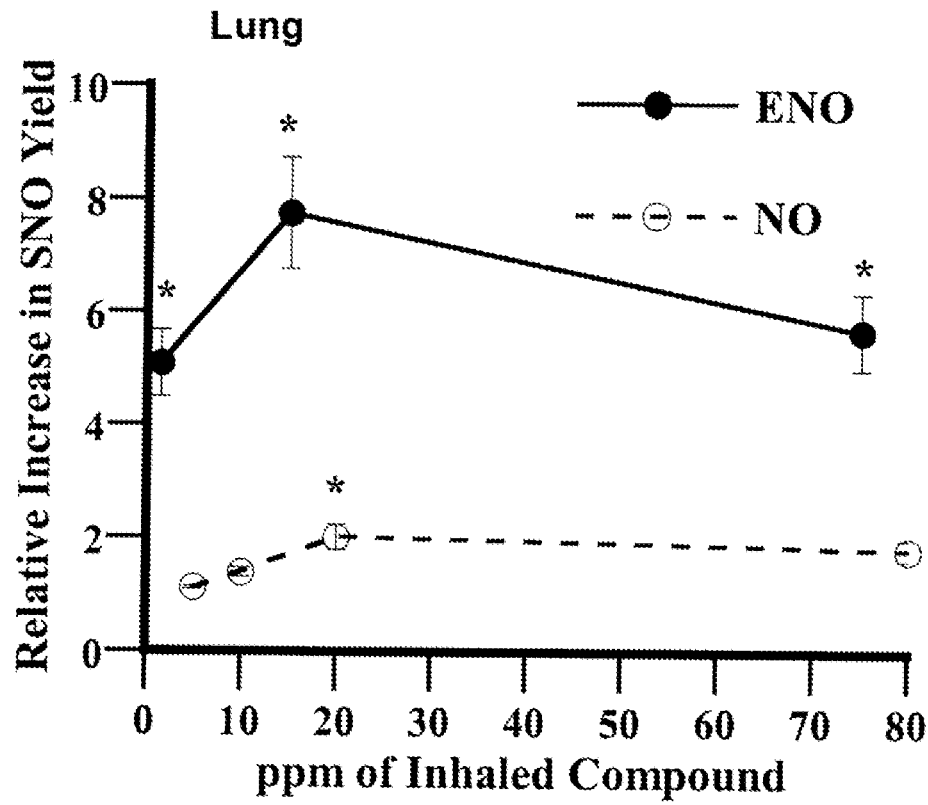
FIGS. 1(A-B) illustrate plots showing inhalation of ENO significantly increases GSNO levels in the lungs (A; several fold over inhaled NO) and also significantly increases SNO-Hb levels in the blood of humans (B).

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "post-acute COVID-19", "post-acute sequelae SARS-CoV infection", or "PASC" refers to persistent symptoms and/or delayed or long-term complications of corona infection, such as SARS-CoV-2 infection, beyond 4 weeks from the onset of symptoms. It is further divided into two categories: (1) subacute or ongoing symptomatic SARS-CoV infection, which includes symptoms and abnormalities present from 4-12 weeks beyond acute COVID-19 or coronavirus infection, such as SARS-CoV-2 infection; and (2) chronic or post-COVID-19 syndrome or coronavirus infection, which includes symptoms and abnormalities persisting or present beyond 12 weeks of the onset of acute COVID-19 or coronavirus infection and not attributable to alternative diagnoses.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

The terms "prevent," "preventing," or "prevention" are art-recognized and include precluding, delaying, averting, obviating, forestalling; stopping, or hindering the onset, incidence, severity, or recurrence of a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the therapeutic compositions described herein. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to compositions and methods for in vivo blood and lung SNO repletion and to their use in treating coronavirus infection, such as severe acute respiratory coronavirus 2 (SARS-CoV-2) infection, coronavirus disease, such as COVID-19, and post-acute COVID or post-acute sequelae of SARS-CoV-2 infection (PASC). The compositions and methods described herein can also be used in methods of treating viral mediated respiratory distress associated with coronavirus infection.

In some embodiments, the methods can include administering to a subject having a coronavirus infection or COVID-19 a therapeutically effective amount of an agent that promotes, increases, and/or induces hemoglobin nitrosylation within red blood cells (RBCs) and GSNO levels in the lungs or airways of the subject. The administration of an agent that promotes, increases, and/or induces hemoglobin nitrosylation within red blood cells (RBCs) and GSNO levels in the lungs or airways of the subject can reduce and/or attenuate at least one component of, and preferentially the whole novel syndrome comprised of viral injury, inflammation, peripheral tissue hypoxemia/hemodynamic instability, microvascular blood flow disorder or an SNO-hemoglobin deficiency like state, associated with and/or caused by the coronavirus infection.

The lung mediates gas exchange between blood and the local atmosphere. However, coronavirus infected patients can die with about 50% blood oxygen saturations. This is because oxygen delivery to tissues is primarily determined by tissue blood flow, not blood oxygen content. Tissue blood flow is controlled by a physiological response termed hypoxic vasodilation in which red blood cells (RBCs) release vasodilator SNO under tissue hypoxia; RBCs thereby increase local blood flow to meet tissue oxygen requirements. Mechanistically, hemoglobin (Hb) is the primary source of SNO in RBCs (so called SNO-Hb) and releases SNO under hypoxia (i.e., when Hb is in the deoxy state). SNO-Hb thus serves as a hypoxia responsive transducer of vasodilatory SNO signals. In addition, uptake of oxygen by RBCs is similarly controlled by SNO-Hb through effects on ventilation-perfusion matching. In essence, the uptake and release of SNOs is a central component of the physiologic response to hypoxia and critical to tissue oxygenation status as part of a 3-gas respiratory cycle (oxygen/NO/carbon dioxide). Importantly, absent SNO in Hb, tissues cannot get adequate amounts of oxygen irrespective of Hb oxygen saturation.

RBC SNO levels in humans are directly linked to, and regulated (allosterically) by, oxygen saturation. This is a key component of the human respiratory cycle through which RBC SNOs control tissue blood flow. Notably, both acute and chronic reductions in oxygenation produce profound declines in circulating SNO-Hb. Further, any restoration of RBC-SNO should preserve allosteric regulation of vasodilation.

The re-conceptualization of the respiratory cycle as a three-gas system provides an explanation for why increasing blood oxygen content alone can fail to improve tissue oxygenation. Tissue blood flow, not blood oxygenation, is the primary determinant of oxygen delivery. Reductions in oxygenation produce profound declines in circulating SNO bioactivity. Conversely aberrant S-nitrosylation (low SNO) can negatively impact both oxygen exchange and oxygen delivery. In this context, it is important to appreciate the profound implications of current treatment guidelines for ventilating COVID-19 patients that target an arterial oxygen saturation of >90% without accounting for SNO status. Such conditions are not conducive to maximizing RBC SNOs and thus improving oxygen delivery.

Respiratory distress mediated by viral injury, such as coronavirus injury to the pulmonary parenchyma, can include shunting and V/Q mismatch resulting in hypoxemia. Administration of an agent, which is able to increase SNOs in both airways and blood, such as SNO-generating compound ethyl nitrite (ENO), to subjects with viral associated respiratory distress by, for example, inhalation (unlike inhaled NO) can increase tissue oxygenation in a setting of reduced oxygen availability. Further, SNO generating compounds can prevent lung injury and inflammation in animal models, and SNOs, such as those generated by ENO administration, have significant anti-viral activity against various coronaviruses.

Moreover, a main form of NO bioactivity in the lungs is GSNO that is maintained enzymatically. GSNO is a potent S-nitrosylating agent that is endowed with bronchodilator, anti-inflammatory, anti-apoptotic, anti-microbial and antiviral activity. GSNO is thus a major component of the innate immune response. GSNO is also important for immune cell function and levels appear to decline in airway disease. Endogenous SNOs, and S-nitrosylation more generally, have been found to inhibit coronavirus infection, suggesting pan viral activity. This supports the use of SNO generating compounds to improve physiologic status in settings of reduced oxygen availability and lung injury. Notably, administration of a SNO generating compound, such as ENO, repletes GSNO levels in airways, as well as SNO-hemoglobin in blood (SNO-Hb, the main regulator of oxygen delivery in the microvasculature via blood flow), which shows clinical utility in treating coronavirus infections, such as SARS-CoV-2 infection, the related lung injury, and deficits in systemic oxygenation.

Furthermore, COVID-19 has been shown to cause widespread microvascular blood flow occlusion. Symptoms of PASC, such as such as fatigue, dyspnea, chest pain, chronic malaise, diffuse myalgia, depressive symptoms and non-restorative sleep, arthralgia, migraine-like headaches, cognitive impairment, including brain fog, which may manifest as difficulties with concentration, memory, receptive language and/or executive function, can be attributed to and/or associated with microvascular blood flow occlusion. Small blood vessel flow is controlled by SNO-Hb in RBCs and SNO donor or generating agents can be effective in repleting and enhancing SNO-Hb and microvascular blood flow in situ without excessively oxidizing hemogloblin or disrupting its allosteric regulation by oxygen.

Therefore, in some embodiments an agent that promotes, increases, and/or induces hemoglobin nitrosylation and GSNO levels in the lung or airways of a subject can be administered to a subject with respiratory distress mediated by viral injury, coronavirus infection, and/or PASC to restore SNO-regulated control over oxygen exchange and delivery, airway/vascular tone, peripheral tissue oxygenation and blood flow, as well as treat lung inflammation and lung injury and improve host defense.

In other embodiments, an agent that promotes, increases, and/or induces hemoglobin nitrosylation and GSNO levels in the lung or airways of the subject can be administered to a subject with respiratory distress mediated by viral injury, coronavirus infection, and/or PASC at an amount effective to promote, improve, and/or enhance microvascular blood flow and/or treat symptoms of PASC, such as such as fatigue, dyspnea, chest pain, chronic malaise, diffuse myalgia, depressive symptoms, non-restorative sleep, arthralgia, migraine-like headaches, and cognitive impairment, including brain fog, which may manifest as difficulties with concentration, memory, receptive language and/or executive function.

In some embodiments, the agent is a SNO generating compound that increases hemoglobin nitrosylation within RBCs and GSNO levels in the lungs of the subject. The SNO generating compound can include a red blood cell and/or hemoglobin nitrosylating compound that does not directly release NO or a related redox species that provides nitric oxide bioactivity, that is activity which is identified with nitric oxide, e.g., vasorelaxation or stimulation or inhibition of a receptor protein, e.g., ras protein, adrenergic receptor, NFκB, Band 3. These compounds are of particular interest as they influence an alternative NO signaling pathway that involves the oxidation of NO or reactions of NO with protein thiols to form S-nitrosothiols (SNOs), which can function as vasodilators.

It is believed that SNO generating compounds that do not directly release NO can interact with hemoglobin to form S-nitrosohemoglobin (SNO-Hb), where its vasodilator potential enables selective delivery of oxygenated blood to hypoxic tissue, organs, and body parts. Because S-nitrosylation is an alternative pathway mediating many NO biological effects, treatment with SNO generating compounds that do not directly release NO may better protect a subject from respiratory distress mediated or associated with viral infection.

In other words, these compounds do not generate pure NO upon administration, which would likely be eliminated by reactions at the hemes of hemoglobin, and likely react with $O_2$ and superoxide to form toxic NOx. Rather, SNO generating compounds that promote or increase hemoglobin nitrosylation and GSNO levels and that do not directly release NO refers to compound that nitrosylates the thiols of hemoglobin and/or of glutathione—and preferentially both, the former in RBCs the latter in lungs—or that is metabolized into compounds that would nitrosylate both thiols efficiently.

In some embodiments, the SNO generating compound is ethyl nitrite (ENO). Advantageously, ENO uniquely generates SNOs in lungs and blood and can be used to treat coronavirus infection, such as severe acute respiratory coronavirus 2 (SARS-CoV-2) infection, coronavirus disease, such as COVID-19, and post-acute COVID or post-acute sequelae of SARS-CoV-2 infection (PASC). Ethyl nitrite does not release NO but rather transfers its NO group to thiols to form SNO. Hence, ethyl nitrite is a nitrosylating agent that does not directly release NO. Ethyl nitrite does not react with $O_2$ or superoxide. One can measure the efficiency of SNO formation exhibited by compounds in vitro and in vivo (e.g., SNO-Hb production) vs. NOx formation. NO itself is be inefficient at nitrosylating thiols, is inactivated by blood hemoglobin, and forms NOx. Conversely, ethyl nitrite for example forms bioactive SNO, including SNO-hemoglobin but not NOx. Furthermore, ethyl nitrite administered by gas raises GSNO in lungs and SNO-Hb in blood.

Ethyl nitrite is available commercially, e.g., diluted in ethanol. Ethyl nitrite (ENO) is a relatively low-molecular-weight colorless organic nitrite with a density of 0.9. ENO is highly volatile and readily decomposes in biologic mediums to produce endogenous mediators of NO bioactivity. Ethyl nitrite forms S-nitrosothiols more readily than does NO, and resists higher-order NO formation.

ENO can be administered by inhalation, ventilation, or insufflation in an amount of 0.1 to 2,000 ppm, preferably 0.1 to 1,000 ppm, more preferably 1 to 200 ppm ENO, and even more preferably 50 to 200 ppm.

It will be appreciated that other nitrosylating agents can be used as SNO generating compounds, but that such nitrosylating compounds should be capable of tranversing the RBC membrane and otherwise specifically reacting with Hb Cys thiols without excessively oxidizing the hemes of hemoglobin to produce toxic amounts of metHb.

In some embodiments, the SNO generating compound is administered to the subject by inhalation, ventilation, or insufflation. For example, when a SNO generating compound is ethyl nitrite (ENO), the administration of ENO by inhalation can be accomplished by a delivery device designed for this purpose.

In other embodiments, the SNO generating compound can be administered by intra or extra vascular aeration. Intravascular aeration refers to the technique where a catheter is placed in a large vein. Such a catheter typically contains a cylindrical bundle of microporous hollow fiber membranes woven into a mat at the end. The catheter is placed within the central venous blood stream in the primary vein that returns blood to the heart (e.g., the inferior vena cava).

In some embodiments, the catheter is initially inserted percutaneously or via open venotomy into a large peripheral vessel (e.g., the femoral vein) and then threaded into the inferior vena cava where the hollow fibers encounter all the blood flowing back to the heart. A respiratory system can activated and ENO along with oxygen ($O_2$) flows from a console outside the patient, through the catheter and through the hollow fibers. The fiber membranes are permeable to gases. As a result, ENO can nitrosylate the blood components to increase NO bioactivity and $O_2$ diffuses into the blood stream from the fibers, while carbon dioxide ($CO_2$) diffuses out of the blood stream into the fibers. Excess ENO, $O_2$ and the "expired" $CO_2$ are transported back through the catheter to the external console.

Extravascular aeration refers to using a device such as an extracorporeal membrane oxygenation (ECMO) machine used on a donor or body part or a subject in need of organ transplantation or placing a donor or subject in need of organ preservation on cardio pulmonary bypass (CPB). An ECMO is an extracorporeal technique of providing both cardiac and respiratory support to patients whose heart and lungs are so severely diseased or damaged that they can no longer serve their function (e.g., see U.S. Pat. No. 7,473,239). For both ECMO and CPB the same concepts of intravascular aeration apply (i.e., administration of ENO and $O_2$ into the circulating blood and removal of $CO_2$).

In other embodiments, the ENO can be provided in a composition or formulation with an agent that potentiates the SNO generating activity of ENO. Such agents can include a thiol based compound, such as, N-acetylcysteine, that can be readily formulated with ENO for inhalation and/or intravenous administration. N-acetylcysteine refers to Acetylcysteine, the N-acetyl derivative of the amino acid L-cysteine, and is a precursor in the formation of the anti-oxidant glutathione in the body. The thiol (sulfhydryl) group confers anti-oxidant effects and is able to reduce free radicals. N-acetylcysteine is soluble in water and alcohol, and practically insoluble in chloroform and ether.

In other embodiments, an agent that promotes, increases, and/or induces hemoglobin nitrosylation within RBCs and GSNO levels in the lung or airways of the subject can include an agent capable of increasing the expression of GSNO and/or inhibiting the catabolic activity of GSNOR in a subject. Examples of GSNO promoting agents described herein include ADH inhibitors, such as GSNOR inhibitors, AKR inhibitors, and SNO-CoAR inhibitors as well as SNO-CoA (or derivatives thereof e.g., SNO-cystamine). Administration of ADH inhibitors, AKR inhibitors, and/or SNO-CoAR inhibitors as well as SNO-CoA (or derivatives thereof e.g., SNO-cystamine) to a subject in need thereof can raise hemoglobin nitrosylation within RBCs and GSNO levels in the subject and treat the coronavirus infection and/or viral mediated respiratory distress.

In some embodiments, the GSNO promoting agent can be a GSNOR inhibitor (also known as an ADH5 inhibitor) or an AKR inhibitor or a thioredoxin inhibitor. In one example, the GSNOR inhibitor can include a pyrrole inhibitor of GSNOR. In some embodiments, the pyrrole inhibitor of GSNOR can be a compound having the following formula:

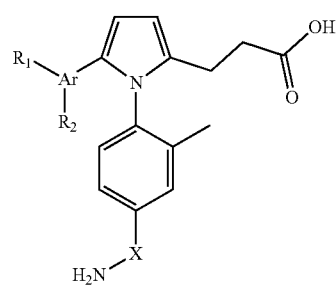

or pharmaceutically acceptable salts, stereoisomers, prodrug, or metabolites thereof;

wherein Ar is an aryl, such as a phenyl and thiophenyl;

$R_1$ is selected from the group consisting of unsubstituted or substituted imidazolyl, chloro, bromo, fluoro, hydroxy, and methoxy;

$R_2$ is selected from the group consisting of hydrogen, methyl, chloro, fluoro, hydroxy, methoxy, ethoxy, propoxy, carbamoyl, dimethylamino, amino, formamido, and trifluoromethyl; and X is selected from the group consisting of CO and $SO_2$.

One example of an ADH5 inhibitor/GSNOR pyrrole inhibitor is GSNOR pyrrole inhibitor N6022, which is commercially available from Nivalis Therapeutics, Boulder, Colo. N6022 has the following formula:

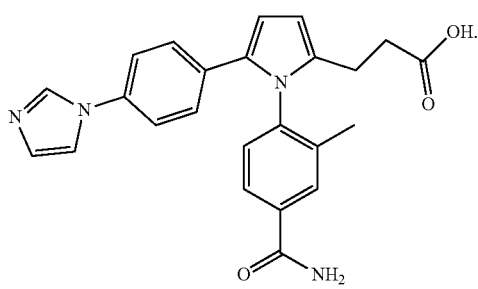 [SMILES: Cc1cc(C(N)=O)ccc1-n1c(CCC(=O)O)ccc1-c1ccc(-n2ccnc2)cc1]

Additional inhibitors of GSNOR for use in methods described herein are disclosed in U.S. Patent Application Publication Nos: 2011/0136875, 2011/0136881, 2011/0144110, 2011/0144180, 2012/0245210, 2013/0253024, 2014/0057957, 2014/0113938, 2014/0113945, 2014/0155447, 2014/0194425, 2014/0194481 and U.S. Pat. Nos. 8,470,857, 8,642,628, 8,673,961, 8,686,015, 8,691,816, 8,759,548, 8,846,736, 8,957,105, 9,029,402, 9,138,427, and 9,180,119 all of which are incorporated herein by reference in their entirety.

Other ADH inhibitors that can be used as a GSNO promoting agent can include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, O-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2,2-trichloroethanol, 4,5-diaminopyrazole and its derivatives and 2-ethyl-5-methyl-2H-3,4-diaminopyrazole. See U.S. Patent Application Publication US 2003/0138390, which is incorporated herein by reference in its entirety.

Fomepizole (4-methylpyrazole) is also a competitive inhibitor of ADH. Pyrazole and its 4-substituted derivatives competitively inhibit the binding of alcohol substrates through the formation of a tight enzyme NAD+ inhibitor complex, in which pyrazole nitrogens interact with both zinc and NAD+. Xie et al., J. Biol. Chem., 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., J. Med. Chem., 37:392-9 (1994), herein incorporated by reference.

Still other ADH inhibitors include dimethyl sulfoxide, Perlman and Wolff, Science, 160:317-9 (1968); and p-methylbenzyl hydroperoxide, Skursky et al., Biochem Int., 26:899-904 (1992), herein incorporated by reference.

In some embodiments, the ADH inhibitor can be a selective ADH6 inhibitor or partially selective ADH6 inhibitor that does not inhibit ADH3. In other embodiments, the ADH inhibitor does not inhibit ADH3 but inhibits other ADHs, such as ADH6.

In some embodiments, the AKR inhibitor can be a selective AKR1A1 inhibitor or a partially selective AKR1A1 that can inhibit other aldo-keto reductase family members, such as AKR1B1. In some embodiments, the AKR1A1 inhibitor can have an IC50≤100 nM. In other embodiments, the AKR1A1 inhibitor can have a selectivity for AKR1A1 versus AKR1B1≥10 times. In other embodiments, the AKR1A1 inhibitor can have a selectivity for AKR1A1 versus other AKRs≥50 times. In still other embodiments, the AKR1A1 inhibitor can have an AKR1A1 IC50≤25 nM and an AKR1B1/AKR1A1 IC50≤300 nM (e.g., less than 100 nM).

Examples of selective and partially selective AKR1A1 inhibitors can include Imirestat (2,7-Difluoro-2'H,5'H-spiro[fluorene-9,4'-imidazolidine]-2',5'-dione) and analogues thereof.

In some embodiments, the imirestat analogues can include compounds selected from the group consisting of:

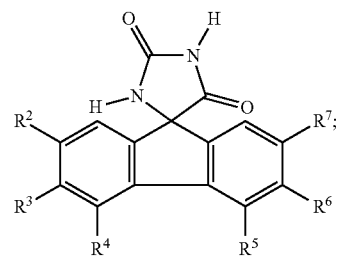

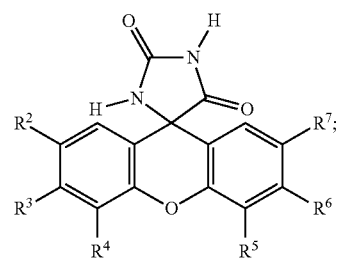

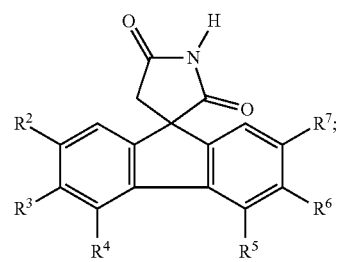

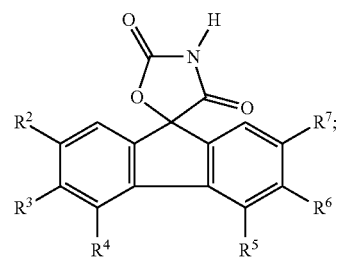

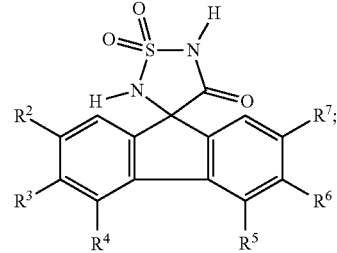

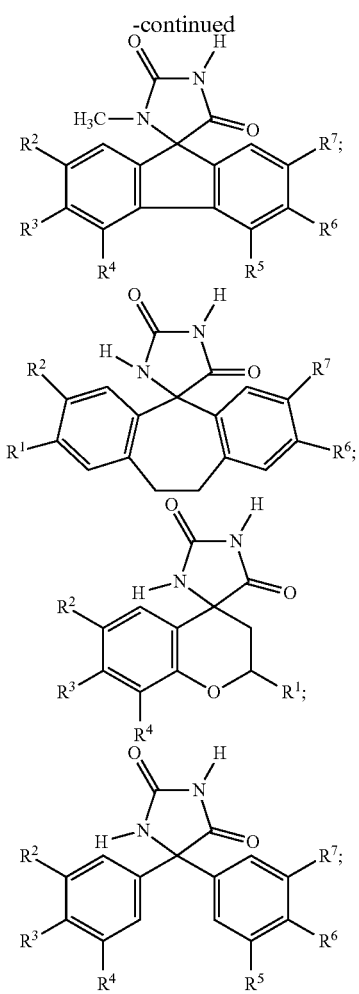

each $R^1$, $R^2$, $R^3$, $R^4$, $R^5$, $R^6$, and $R^7$ are the same or different and are one or more substituent selected from the group consisting of hydrogen, halogen, substituted or unsubstituted C1-C24 alkyl, C2-C24 alkenyl, C2-C24 alkynyl, C3-C20 aryl, heterocycloalkenyl containing from 5-6 ring atoms, (wherein from 1-3 of the ring atoms is independently selected from N, NH, N(C1-C6 alkyl), NC(O)(C1-C6 alkyl), O, and S), heteroaryl or heterocyclyl containing from 5-14 ring atoms, (wherein from 1-6 of the ring atoms is independently selected from N, NH, N(C1-C3 alkyl), O, and S), C6-C24 alkaryl, C6-C24 aralkyl, halo, silyl, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), C2-C24 alkylcarbonato (—O—(CO)—O-alkyl), C6-C20 arylcarbonato (—O—(CO)-O-aryl), carboxy (—COOH), carboxylato (—COO—), carbamoyl (—(CO)—NH2), C1-C24 alkyl-carbamoyl (—(CO)—NH(C1-C24 alkyl)), arylcarbamoyl (—(CO)—NH-aryl), thiocarbamoyl (—(CS)—NH2), carbamido (—NH—(CO)—NH2), cyano(—CN), isocyano (—N+C—), cyanato (—O—CN), isocyanato (—O—N+=C—), isothiocyanato (—S—CN), azido (—N=N+=N—), formyl (—(CO)—H), thioformyl (—(CS)—H), amino (—NH2), C1-C24 alkyl amino, C5-C20 aryl amino, C2-C24 alkylamido (—NH—(CO)-alkyl), C6-C20 arylamido (—NH—(CO)-aryl), sulfanamido (—SO2NR2 where R is independently H, alkyl, aryl or heteroaryl), imino (—CR=NH where R is hydrogen, C1-C24 alkyl, C5-C20 aryl, C6-C24 alkaryl, C6-C24 aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO2), nitroso (—NO), sulfo (—SO2—OH), sulfonato (—SO2—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO2-aryl), sulfonamide (—SO2—NH2, —SO2NY2 (wherein Y is independently H, aryl or alkyl), phosphono (—P(O)(OH)2), phosphonato (—P(O)(O—)2), phosphinato (—P(O)(O—)), phospho (—PO2), phosphino (—PH2), polyalkyl ethers (—[(CH2) nO]m), phosphates, phosphate esters [—OP(O)(OR)2 where R=H, methyl or other alkyl], groups incorporating amino acids or other moieties expected to bear positive or negative charge at physiological pH, and combinations thereof; and pharmaceutically acceptable salts thereof.

Other examples of selective and partially selective AKR1A1 inhibitors can include Methyl[4-oxo-2-(substituted benzoylimino)-3-(substituted phenyl)thiazolidin-5-ylidene]acetate derivatives recited in S. Ali et al., "Design, synthesis and molecular modeling of novel methyl[4-oxo-2-(aroylimino)-3-(substituted phenyl)thiazolidin-5-ylidene] acetates as potent and selective aldose reductase inhibitors", Med. Chem. Commun., 2012, 3, 1428-1434. These AKR1A1 inhibitors can have the following formula:

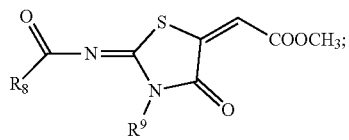

wherein $R^8$ and $R^9$ are independently selected from the group consisting of substituted and unsubstituted aryls.

Other examples of selective and partially selective AKR1A1 inhibitors can include benzothiazolyl substituted iminothiazolidinones and benzamido-oxothiazolidines recited in Saeed et al., "Benzothiazolyl substituted iminothiazolidinones and benzamido-oxothiazolidines as potent and partly selective aldose reductase inhibitors", Med. Chem. Commun., 2014, 5, 1371-1380. These AKR1A1 inhibitors can have the following formula:

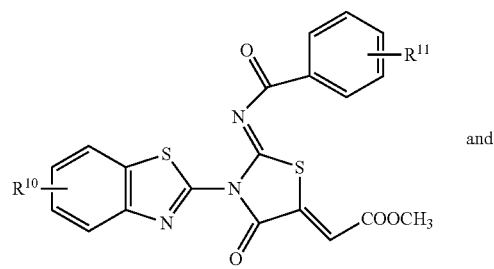

and

-continued

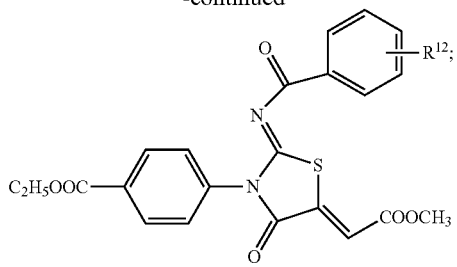

wherein $R^{10}$, $R^{11}$, or $R^{12}$ include one or more substituent and are each independently selected from the group consisting of H, a halogen (e.g., 6-Br, 3-Cl, 2-F, 2-Br, 5,6-di-Cl, 2,4-di-Cl), lower alkyl, and methoxy (e.g., 4-OCH$_3$, 3,4-OCH$_3$).

Still other examples of selective and partially selective AKR1A1 inhibitor are disclosed in the following publications: Mechanism of Human Aldehyde Reductase: Characterization of the Active Site Pocket, Oleg A. Barski et al., Biochemistry 1995, 34, 11264-11275, In vivo role of aldehyde reductase, M. Takahashi et al., Biochim Biophys Acta. 2012 November; 1820(11):1787-96, The Aldo-Keto Reductase Superfamily and its Role in Drug Metabolism and Detoxification, Oleg A. Barski et al., Drug Metab Rev. 2008; 40(4): 553-624, Asborin Inhibits Aldo/Keto Reductase 1A1, Matthias Scholz et al., Chem Med Chem, 2011, 6, 89-93, Inhibition of Aldehyde Reductase by Aldose Reductase Inhibitors, Sanai Sato et al., Biochemical Pharmacology, 1990. 40, 1033-1042, Inhibition of human aldose and aldehyde reductases by non-steroidal anti-inflammatory drugs, D. Michelle Ratliff et al., Advances in Experimental Medicine and Biology, Volume: 463, Issue: Enzymology and Molecular Biology of Carbonyl Metabolism 7, Pages: 493-499 (1999.), Inhibition of aldehyde reductases, Philip J. Schofield et al., Progress in Clinical and Biological Research, 1987, 232, Issue: Enzymol. Mol. Biol. Carbonyl Metab., 287-96, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in vitro Activity, Polyxeni Alexiou et al., J. Med. Chem. 2010, 53, 7756-7766, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in vitro Activity, Polyxeni Alexiou et al., J. Med. Chem. 2010, 53, 7756-7766, all of which are incorporated herein by reference in their entirety. It will be appreciated that any potential selective or partially selective AKR1A1 inhibitors can be used in the compositions and methods recited herein.

In some embodiments, a SNO generating compound can be administered in combination with a GSNOR inhibiting agent (GSNOR inhibitor and/or AKR inhibitor). For example, ENO can be administered by inhalation, ventilation, or insufflation in, for example, an amount of 0.1 to 2,000 ppm in combination with a GSNOR inhibitor, such as an AKR inhibitor or a thioredoxin inhibitor, at an amount effective to promote, increase, and/or induce hemoglobin nitrosylation within RBCs and GSNO levels in the lung or airways of the subject.

In some embodiments, the agent that promotes, increases, and/or induces hemoglobin nitrosylation within RBCs and GSNO levels in the lung or airways of the subject can be provided in pharmaceutical compositions with at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

Pharmaceutical compositions comprising the agent that promotes, increases, and/or induces hemoglobin nitrosylation within RBCs and GSNO levels in the lung or airways of the subject can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc.

Specifically, the agent that promotes, increases, and/or induces hemoglobin nitrosylation within RBCs and GSNO levels in the lung or airways of the subject can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For targeted delivery to a subject's airway or lung tissue in accordance with a method described above, an inhalation formulation can be used to achieve high local concentrations. Formulations suitable for inhalation include dry powder or aerosolized or vaporized solutions, dispersions, or suspensions capable of being dispensed by an inhaler or nebulizer into the endobronchial or nasal cavity of a subject in need thereof. In some embodiments, the agent can be delivered via aerosol spray from pressured container or dispenser that contains a suitable propellant, e.g., a gas such as carbon dioxide, a nebulized liquid, or a dry powder from a suitable device.

By way of example, an ENO Blend (1,000 ppm in nitrogen) can be manufactured by blending ENO liquid API in nitrogen to form an homogeneous gas blend at a concentration of 1000 ppmv (equivalent to a 0.1 mole/mole percent) and pressure of approximately 1800 psi. The blending can be performed gravimetrically and conducted in accordance with current Good Manufacturing Practices and standard compressed gas manufacturing procedures. Other final blend concentrations can be prepared as required.

Solutions or suspensions, which include the agents described herein, used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringe ability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In some embodiments, the agent can be prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions that include the agent that promotes, increases, and/or induces hemoglobin nitrosylation within RBCs and GSNO levels in the lung or airways of the subject can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, silicified microcrystalline cellulose, gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose; lactose such as lactose monohydrate, and lactose anhydrous; dibasic calcium phosphate, mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In some embodiments, the agent that promotes, increases, and/or induces hemoglobin nitrosylation within RBCs and GSNO levels in the lung or airways of the subject can be administered to viral infected subject to reduce and/or attenuate at least one of viral injury, inflammation, peripheral tissue hypoxemia/hemodynamic instability, red blood cell disorder, or an SNO-hemoglobin deficiency like state associated with and/or caused by the viral infection.

In some embodiments, the viral infection can occur with an infection, such as SARS-CoV, MERS-CoV, and SARS-CoV-2, Human Coronavirus 229E, Human Coronavirus OC43. Other viral infections, which can potentially cause viral injury, inflammation, peripheral tissue hypoxemia/hemodynamic instability, red blood cell disorder, or an SNO-hemoglobin deficiency like state, and be treated with the agent include, Canine enteric coronavirus (strain INSAVC-1), Canine enteric coronavirus (strain K378), Feline enteric coronavirus (strain 79-1683), Feline infectious peritonitis virus (FIPV), Human coronavirus 229E, Porcine epidemic diarrhea virus, Porcine epidemic diarrhea virus (strain Br1/87), Porcine epidemic diarrhea virus (strain CV777), Transmissible gastroenteritis virus, Porcine respiratory coronavirus, Porcine transmissible gastroenteritis coronavirus (STRAIN FS772/70), Porcine transmissible gastroenteritis coronavirus (strain Miller), Porcine transmissible gastroenteritis coronavirus (strain Neb72-RT), Porcine transmissible gastroenteritis coronavirus (STRAIN PURDUE), Bovine coronavirus, Bovine coronavirus (STRAIN F15), Bovine coronavirus (strain G95), Bovine coronavirus (STRAIN L9), Bovine coronavirus (strain LSU-94LSS-051), Bovine coronavirus (STRAIN LY-138), Bovine coronavirus (STRAIN MEBUS), Bovine coronavirus (strain OK-0514-3), Bovine coronavirus (strain Ontario), Bovine coronavirus (STRAIN QUEBEC), Bovine coronavirus (STRAIN VACCINE), Bovine enteric coronavirus (strain 98TXSF-110-ENT), Canine respiratory coronavirus, Chicken enteric coronavirus, Human coronavirus OC43, Murine hepatitis virus, Murine coronavirus (strain DVIM), Murine hepatitis virus (strain A59), Murine hepatitis virus (strain JHM), Murine hepatitis virus (strain S), Murine hepatitis virus strain 1, Murine hepatitis virus strain 2, Murine hepatitis virus strain 3, Murine hepatitis virus strain 4, Murine hepatitis virus strain ML-11, Porcine hemagglutinating encephalomyelitis virus, Porcine hemagglutinating encephalomyelitis virus (strain 67N), Porcine hemagglutinating encephalomyelitis virus (strain IAF-404), Puffinosis virus, Rat coronavirus, Rat coronavirus (strain 681), Rat coronavirus (strain NJ), Rat sialodacryoadenitis coronavirus, Turkey coronavirus, Turkey coronavirus (strain Indiana), Turkey coronavirus (strain Minnesota), Turkey coronavirus (strain NC95), Avian infectious bronchitis virus, Avian infectious bronchitis virus (STRAIN 6/82), Avian infectious bronchitis virus (strain Arkansas 99), Avian infectious bronchitis virus (strain Beaudette CK), Avian infectious bronchitis virus (strain Beaudette M42), Avian infectious bronchitis virus (strain Beaudette US), Avian infectious bronchitis virus (strain Beaudette), Avian infectious bronchitis virus (strain D1466), Avian infectious bronchitis virus (strain D274), Avian infectious bronchitis virus (strain D3896), Avian infectious bronchitis virus (strain D41), Avian infectious bronchitis virus (strain DE072), Avian infectious bronchitis virus (strain GRAY), Avian infectious bronchitis virus (strain H120), Avian infectious bronchitis virus (strain H52), Avian infectious bronchitis virus (strain KB8523), Avian infectious bronchitis virus (strain M41), Avian infectious bronchitis virus (strain PORTUGAL/322/82), Avian infectious bronchitis virus (strain SAIB20), Avian infectious bronchitis virus (strain UK/123/82), Avian infectious bronchitis virus (strain UK/142/86), Avian infectious bronchitis virus (strain UK/167/84), Avian infectious bronchitis virus (strain UK/183/66), Avian infectious bronchitis virus (strain UK/68/84), Avian infectious bronchitis virus (strain V18/91), Avian infectious bronchitis virus (strain Vic S), Avian infectious laryngotracheitis virus, SARS coronavirus, SARS coronavirus Beijing ZY-2003, SARS coronavirus BJ01, SARS coronavirus BJ02, SARS coronavirus BJ03, SARS coronavirus BJ04, SARS coronavirus CUHK-Su10, SARS coronavirus CUHK-W1, SARS coronavirus Frankfurt 1, SARS coronavirus GZ01, SARS coronavirus HKU-39849, SARS coronavirus Hong Kong ZY-2003, SARS coronavirus Hong Kong/03/2003, SARS coronavirus HSR 1 SARS coronavirus Sin2500, SARS coronavirus Sin2677, SARS coronavirus Sin2679, SARS coronavirus Sin2748, SARS coronavirus Sin2774, SARS coronavirus Taiwan, SARS coronavirus Taiwan JC-2003, SARS coronavirus Taiwan TC1, SARS coronavirus Taiwan TC2, SARS coronavirus Tor2, SARS coronavirus TW1, SARS coronavirus TWC, SARS coronavirus Urbani, SARS coronavirus Vietnam, SARS coronavirus ZJ-HZ01, SARS coronavirus ZJ01 Bovine respiratory coronavirus (strain 98TXSF-110-LUN), Human enteric coronavirus 4408, Enteric coronavirus, Equine coronavirus, and Equine coronavirus NC99.

In some embodiments, pharmaceutical compositions comprising the agent that promotes, increases, and/or induces hemoglobin nitrosylation within RBCs and GSNO levels in the lung or airways of the subject can be used for prophylactic therapy. For example, a therapeutically effective amount of the agent that promotes, increases, and/or induces hemoglobin nitrosylation in RBCs and GSNO levels in the lung or airways of the subject can be administered to a viral infected subject in need thereof prior to oxygen exposure or during daily oxygen exposure to treat respiratory distress. In certain embodiments, subjects can include viral infected human patients experiencing treatment with prolonged supplemental oxygen.

In some embodiments, the therapeutically effective amount is an amount effective to provide improvements in pulmonary function, oxygenation parameters, and hemodynamic stability. In addition to quantifying changes in SNO-Hb, standard bio-markers (d-dimer, ferritin, CRP, and troponins) along with CBC differential, degree of lymphopenia and viral load can be measured to determine therapeutic efficacy.

In still other embodiments, the therapeutically effective amount is the amount required to decrease by at least 1%, 5%, 10%, 20%, 30%, 40%, 50%, 60%, 70%, 80%, 90%, or even completelyl reverse airway hyperreactivity observed in a subject with viral infection.

In some embodiments, the therapeutically effective amount can be the amount required to increase lung compliance (Crs) at least 1%, 5%, 10%, 20%, 30%, 40%, 50%, 60%, 70%, 80%, 90%, or more and/or decrease lung respiratory resistance (Rrs) associated with hyperoxia in a human subject administered supplemental oxygen by at least 1%, 5%, 10%, 20%, 30%, 40%, 50%, 60%, 70%, 80%, 90%, or more. In some embodiments, the therapeutically effective amount can be the amount required to produce a measurable increase (e.g., at least 1%, 5%, 10%, 20%, 30%, 40%, 50%, 60%, 70%, 80%, 90%, or more) in forced expiratory volume in 1 second (FEV1), forced expiratory flow (FEF2) and/or increased exercise capacity in the subject.

In some embodiments, the agent that promotes, increases, and/or induces hemoglobin nitrosylation within RBCs and GSNO levels in the lung or airways of the subject can be administered in a combinatorial therapy or combination therapy that includes administration of the agent (e.g., SNO generating compound) with one or more additional active agents. The phrase "combinatorial therapy" or "combination therapy" embraces the administration of the agent that promotes, increases, and/or induces hemoglobin nitrosylation within RBCs and GSNO levels in the lung or airways of the subject, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the agent that promotes, increases, and/or induces hemoglobin nitrosylation within RBCs and GSNO levels in the lung or airways of the subject can be administered in combination with active agents, such as vasodilators, prostanoid agonists, antiandrogens, cyclosporins and their analogues, antivirals, triterpenes, anti-fibrosis agents alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5α-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11):1465-1473) or thioredoxin reductase inhibitors, such as auranofin.

In some embodiments, the agent that promotes, increases, and/or induces hemoglobin nitrosylation within RBCs and GSNO levels in the lung or airways of the subject is given together with antivirals, such as Remdesivir.

Antiviral agents that can be used in the compositions and methods described herein can include, for example, substrates and substrate analogs, inhibitors and other agents that severely impair, debilitate or otherwise destroy virus-infected cells. Substrate analogs include amino acid and nucleoside analogs. Substrates can be conjugated with toxins or other viricidal substances. Inhibitors include integrase inhibitors, protease inhibitors, polymerase inhibitors and transcriptase inhibitors such as reverse transcriptase inhibitors.

Antiviral agents that can be used in the compositions and methods described herein can include, for example, ganciclovir, valganciclovir, oseltamivir (Tamiflu), zanamivir (Relenza), abacavir, aciclovir, acalabrutinib, acyclovir, adefovir, amantadine, amprenavir, ampligen, APNO1, arbidol, atazanavir, atripla, azithromycin, boceprevir, camostat, cidofovir, ciclesonide, chloroquine, combivir, dalbavancin, darunavir, delavirdine, didanosine, docosanol, edoxudine, efavirenz, emtricitabine, enfuvirtide, entecavir, famciclovir, favipiravir, fomivirsen, fosamprenavir, foscarnet, fosfonet, fusion inhibitors (e.g., enfuvirtide), hydroxychloroquine, ibacitabine, imunovir, idoxuridine, imiquimod, indinavir, inosine, integrase inhibitor, interferon type III, interferon type II, interferon type I, interferon, ivermectin, lamivudine, lopinavir, loviride, maraviroc, mefloquine, monensin, moroxydine, nelfinavir, nevirapine, nexavir, nucleoside or nucleotide analogues, peginterferon alfa-2a, penciclovir, peramivir, pleconaril, podophyllotoxin, protease inhibitor, oritavancin, raltegravir, Remdesivir, reverse transcriptase inhibitor, ribavirin, rimantadine, ritonavir, pyrimidine antiviral, saquinavir, stavudine, synergistic enhancer (antiretroviral), taribavirin, telcoplanin, tenofovir, tenofovir disoproxil, tipranavir, trifluridine, trizivir, tromantadine, truvada, umifenovir, valaciclovir (Valtrex), vicriviroc, vidarabine, viramidine, zalcitabine, zidovudine, and combinations thereof.

Examples of nucleoside or nucleotide analogs include acyclovir (ACV), ganciclovir (GCV), famciclovir, favipiravir, foscarnet, lopinavir/ritonavir, Remdesivir, ribavirin, zalcitabine (ddC), zidovudine (AZT), stavudine (D4T), lamivudine (3TC), didanosine (ddI), cytarabine, dideoxyadenosine, edoxudine, floxuridine, idozuridine, inosine pranobex, 2'-deoxy-5-(methylamino)uridine, trifluridine and vidarabine. Examples of a few protease inhibitors that show particular promise in human therapy include saquinivir, ritonavir and indinavir. Other anti-viral agents include interferons (e.g., α-, β-, γ-interferon), cytokines such as tumor necrosis factor (TNF), cell receptors, growth factor antagonists, which can be purified or recombinantly produced, and combinations thereof.

Preferably, the known antiviral compounds are selected from the group consisting of Vidarabine, Acyclovir, Ganciclovir, Valganciclovir, Valacyclovir, Cidofovir, Famciclovir, favipiravir, Ribavirin, lopinavir, ritonavir, Amantadine, Rimantadine, Interferon, Oseltamivir, Palivizumab, Rimantadine, Zanamivir, nucleoside-analog reverse transcriptase inhibitors (NRTI) such as Zidovudine, Didanosine, Zalcitabine, Stavudine, Lamivudine and Abacavir, non-nucleoside reverse transcriptase inhibitors (NNRTI) such as Nevirapine, Delavirdine and Efavirenz, protease inhibitors such as Saquinavir, Ritonavir, Remdesivir, Indinavir, Nelfinavir, Amprenavir, other known antiviral compounds and preparations, and combinations thereof.

Other active compounds, which can be present in pharmaceutical compositions include anti-fibrosis agents, such as pirfenidone, and nintedanib, aminexil and its derivatives, 60-[(9Z,12Z)octadec-9,12-dienoyl]hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium panthotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

The invention is further illustrated by the following example, which is not intended to limit the scope of the claims.

EXAMPLE

FIGS. 1-8 of this example together show that ENO and SNOs derived therefrom (GSNO in lungs and SHO-Hb in blood) reverse and protect against coronavirus infection, such as severe acute respiratory coronavirus 2 (SARS-CoV-2) infection, coronavirus disease, such as COVID-19, and post-acute COVID or post-acute sequelae of SARS-CoV-2 infection (PASC): i.e., kill the virus; prevent lung inflammation; and improve peripheral tissue oxygenation.

Methods

ENO Formulation

ENO was prepared solely for our use under good manufacturing procedures by Custom Gas Solutions; Durham, N.C. Tanks were produced at 1000 ppm.

ENO Delivery

1. Mice are either placed in chambers where ambient oxygen and ENO levels (1-100 ppm) are controlled, or mice are ventilated as in 2. below.

2. Large animals (pigs/dogs) are ventilated. ENO was mixed into the ventilation circuit using a custom-made gas-blending device (1-100 ppm). One hundred ppm ENO was selected as the maximum dose based on the amounts of metHb (<5%).

3. Humans Each subject was fitted with an on-demand nonrebreather mask to regulate oxygen ($FiO_2$) and ENO delivery. ENO was blended at 1-100 ppm.

Methods for Measuring SNO-Hb

Photolysis-chemiluminescence was used to quantify RBC SNO-Hb levels before and during ENO exposure. Blood was obtained through arterial lines and venipuncture. Method of sample preparation and measurement is as described in Hausladen (ref: Hausladen A et al. Assessment of nitric oxide signals by triiodide chemiluminescence. *Proc. Natl. Acad. Sci. U.S.A* 104, 2157-2162 (2007)).

Assessment of Lung Inflammation

Bronchoalveolar lavage fluid (BAL), cell and protein content, differential cell analysis, lung fixation and histological sectioning, were performed as previously described (Groves, Am. J. Respir Cell Mol. Biol. 47, 776-783 (2012); Lien Van Hoecke *J Vis Exp.* 2017; (123): 55398)).

Results

Figure 1B:
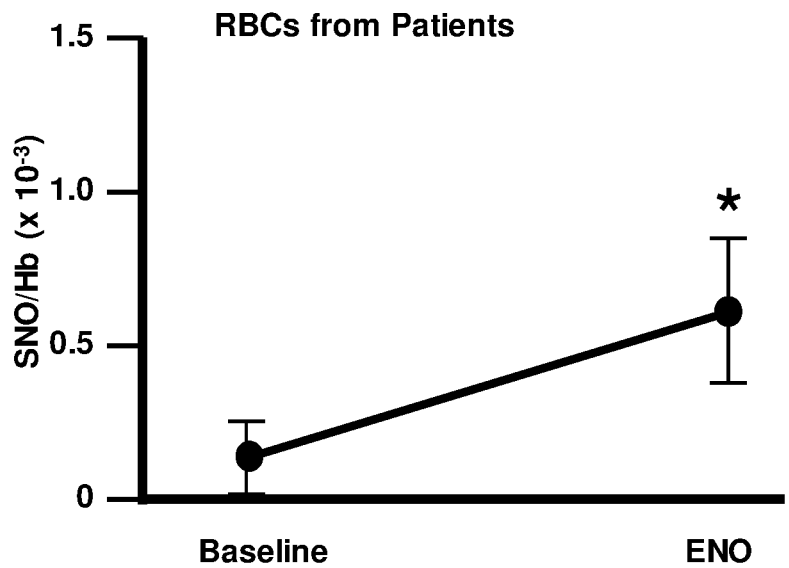

FIGS. 1(A-B) illustrate plots showing inhalation of ENO significantly increases GSNO levels in the lungs (A; several fold over inhaled NO) and also significantly increases SNO-Hb levels in the blood of humans (B).

Figure 2:
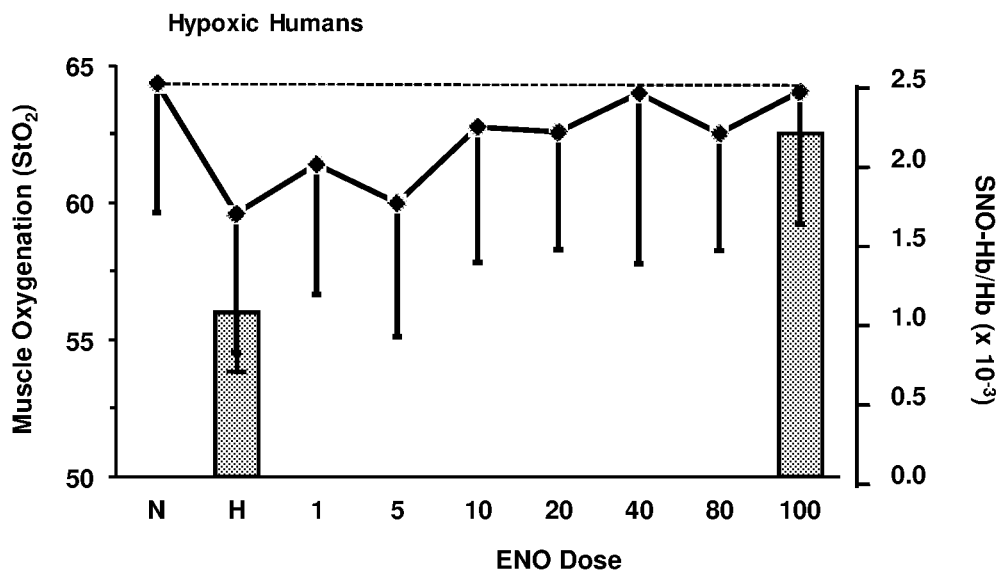
FIG. 2 illustrates a plot showing ENO increases SNO-Hb in hypoxic humans. Human muscle oxygenation (solid line) measured with near infrared spectroscopy during hypoxia and dosing with ENO. At study completion, muscle $StO_2$ was at normoxic (prehypoxic) levels and SNO-Hb levels (grey bars) had doubled while $FiO_2$ was kept fixed at 0.12.

FIG. 2 illustrates a plot showing ENO increases SNO-Hb in hypoxic humans. Human muscle oxygenation (solid line) measured with near infrared spectroscopy during hypoxia and dosing with ENO. At study completion, muscle $StO_2$ was at normoxic (prehypoxic) levels and SNO-Hb levels (grey bars) had doubled while $FiO_2$ was kept fixed at 0.12.

Figure 3A:
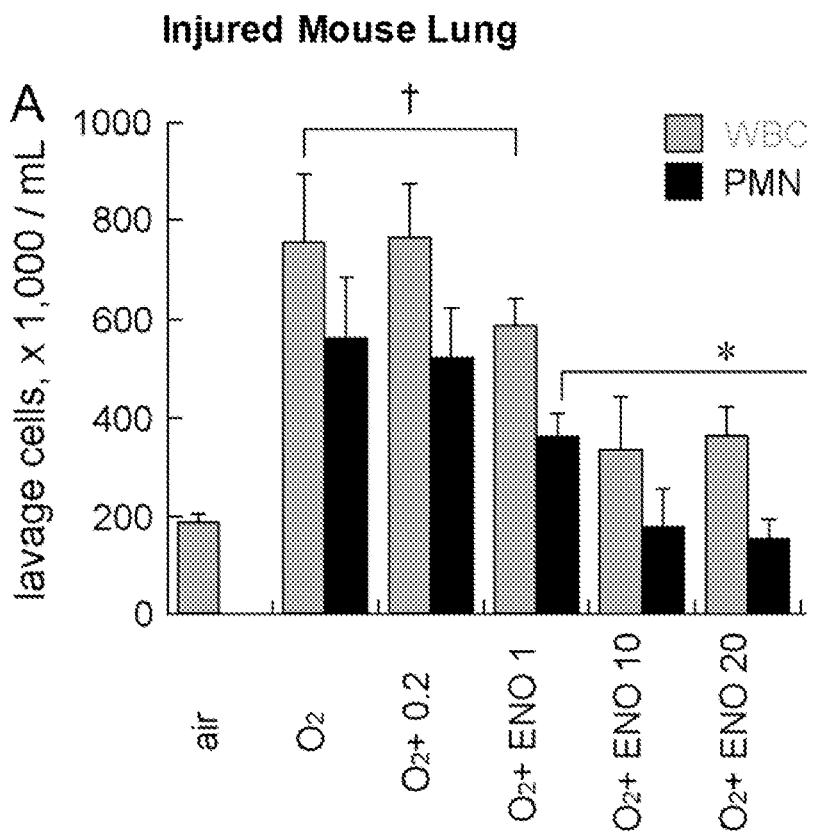
FIGS. 3(A-C) illustrate ENO reduces lung inflammation. Treatment of mice with ENO for 8 days decreased hyperoxic injury-induced lung (BALF) leukocyte and neutrophil concentrations (A). ENO also attenuated the accumulation (B) and expression (C) of cytokine-induced neutrophil chemoattractant-1.
Figure 3B:
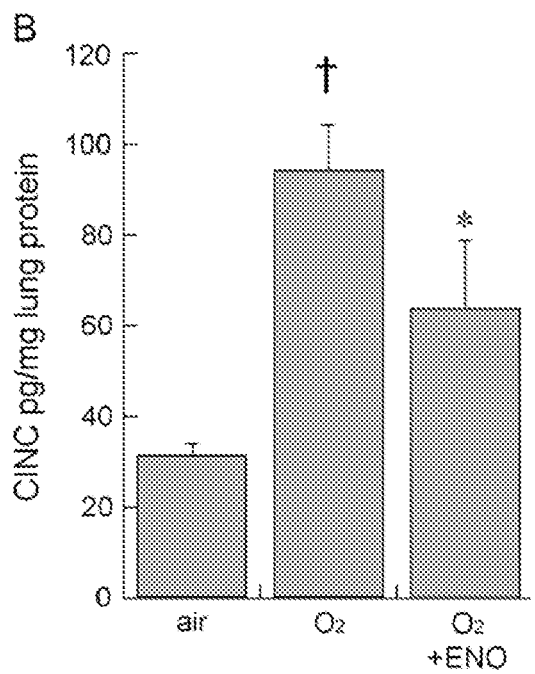
Figure 3C:
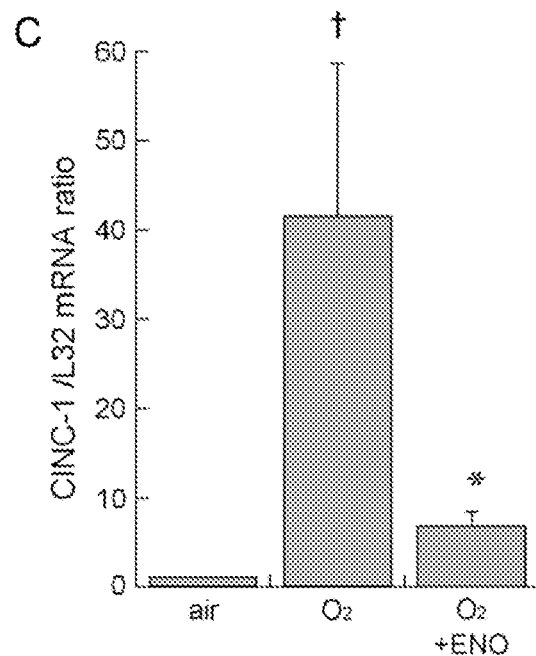

FIGS. 3(A-C) illustrate ENO reduces lung inflammation. Treatment of mice with ENO for 8 days decreased hyperoxic injury-induced lung (BALF) leukocyte and neutrophil concentrations (A). ENO also attenuated the accumulation (B) and expression (C) of cytokine-induced neutrophil chemoattractant-1.

Figure 4A:
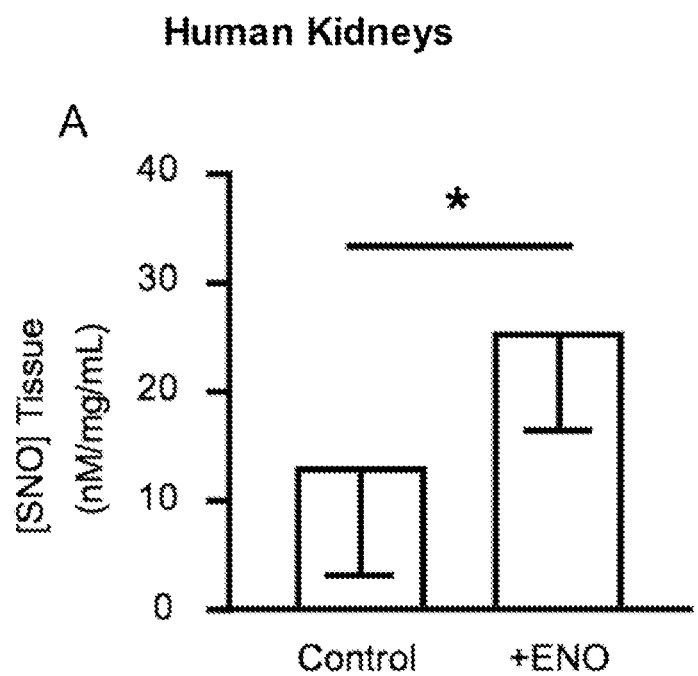
FIGS. 4(A-C) illustrate graphs showing ENO increased tissue SNO levels (A) and the release (B) and level (C) of the anti-inflammatory interleukin, IL-10 in isolated human kidneys.
Figure 4B:
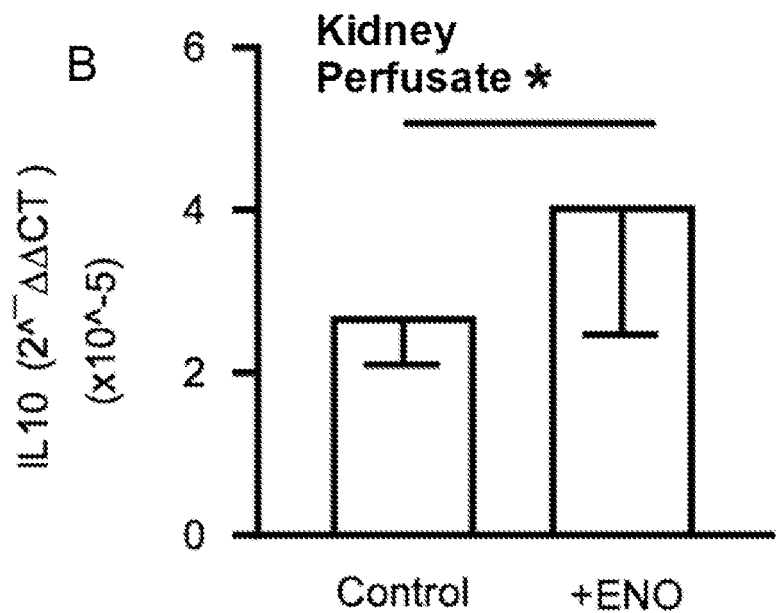
Figure 4C:
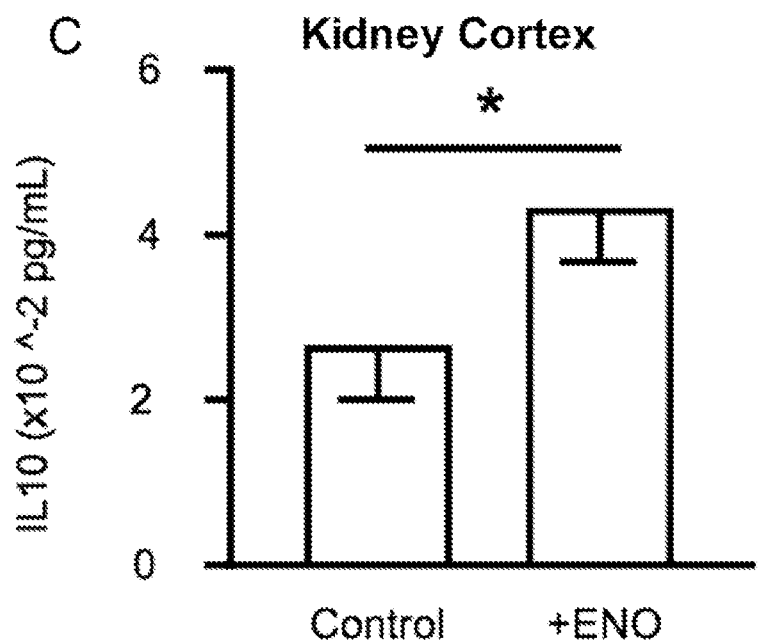

FIGS. 4(A-C) illustrate graphs showing ENO increased tissue SNO levels (A) and the release (B) and level (C) of the anti-inflammatory interleukin, IL-10 in isolated human kidneys.

Figure 5A:
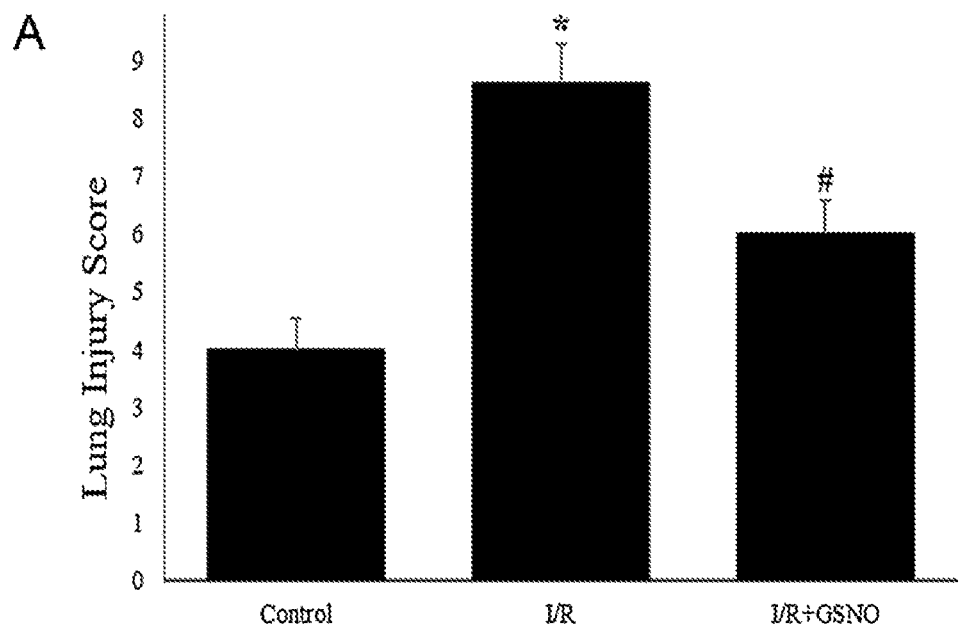
FIGS. 5(A-C) illustrate graphs showing administration of GSNO significantly reduced lung injury (A) and expression of inflammatory markers including (iNOS) (B) and NF-kappaB (C) in a rat ischemia/reperfusion (IR) preparation.
Figure 5B:
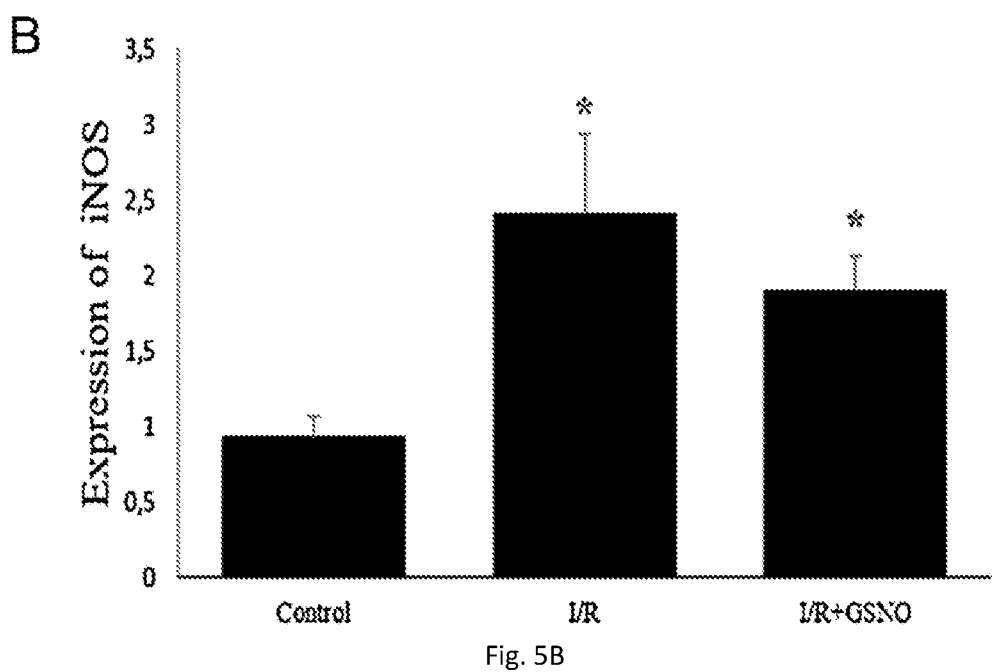
Figure 5C:
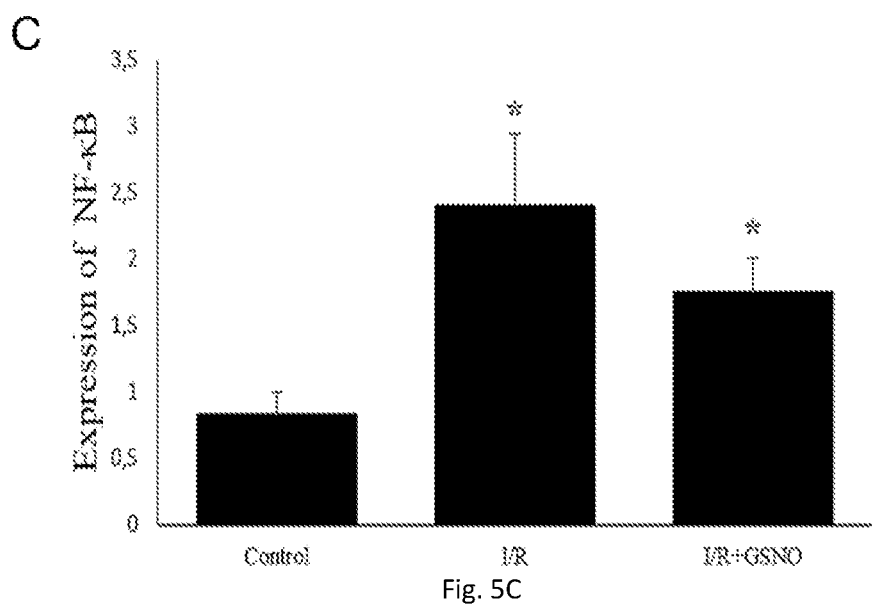

FIGS. 5(A-C) illustrate graphs showing administration of GSNO significantly reduced lung injury (A) and expression of inflammatory markers including (iNOS) (B) and NF-kappaB (C) in a rat ischemia/reperfusion (IR) preparation.

Figure 6:
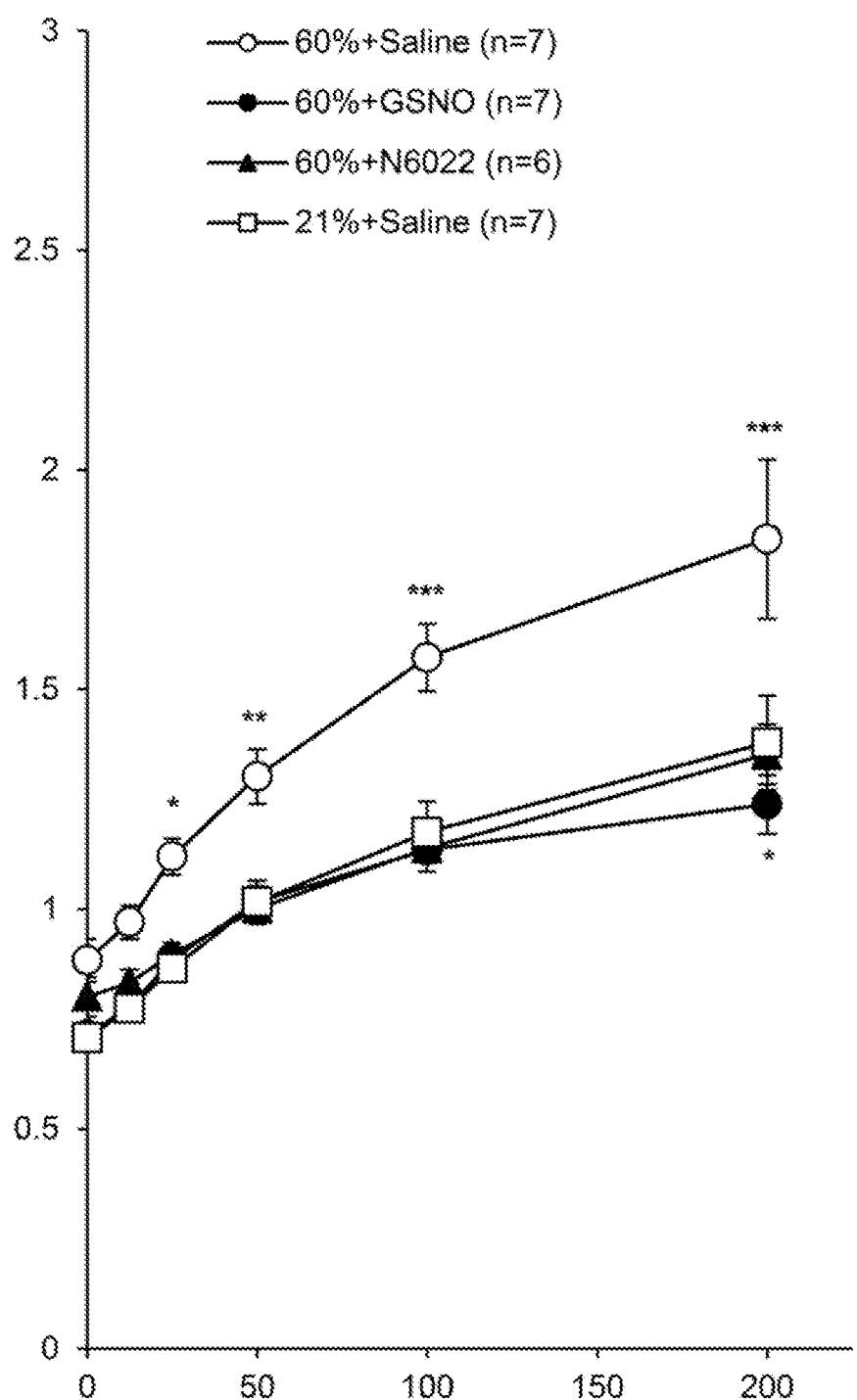
FIG. 6 illustrates a plot showing GSNO improves lung injury. Mouse airway hyper-responsiveness following hyperoxia (60% oxygen for 21 days) is attenuated by inhalation of GSNO or ip administration of the GSNOR inhibitor, N6022, which raises GSNO.

FIG. 6 illustrates a plot showing GSNO improves lung injury. Mouse airway hyper-responsiveness following hyperoxia (60% oxygen for 21 days) is attenuated by inhalation of GSNO or ip administration of the GSNOR inhibitor, N6022, which raises GSNO.

Figure 7A:
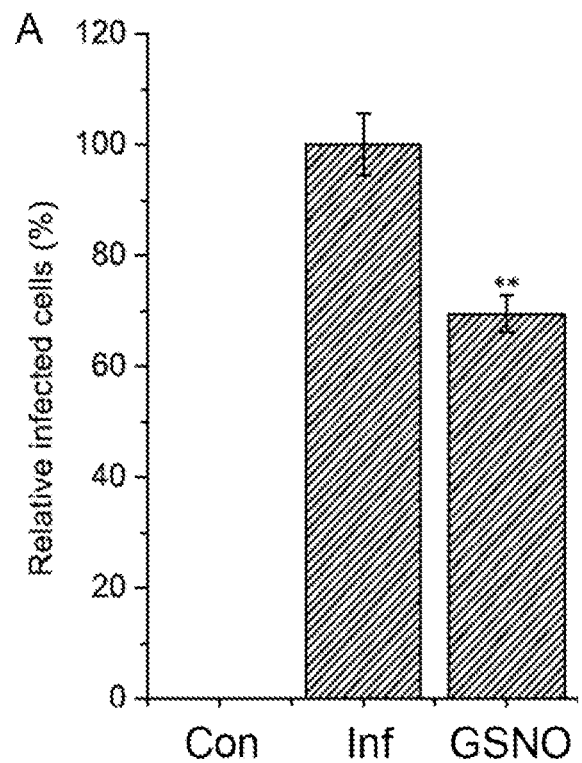
FIGS. 7(A-C) illustrate graphs and a plot showing GSNO has antiviral activity against corona viruses. GSNO significantly reduces infection (Inf; A) and replication (B) of porcine circovirus type 2 (PCV2) (human corona analogue). SNO treatment also significantly reduces viral replication in PCV2-infected mice ((DPI, days post-inoculation; NC, normal control).
Figure 7B:
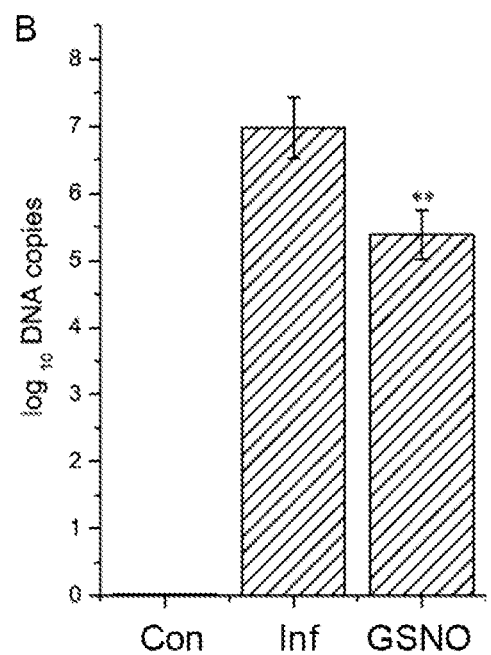
Figure 7C:
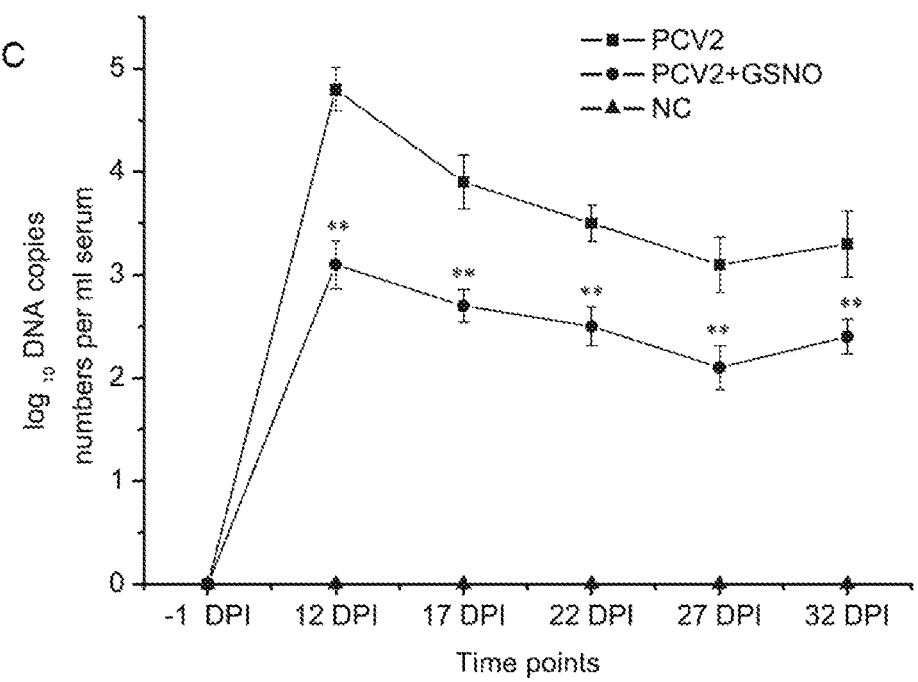
Figure 8A:
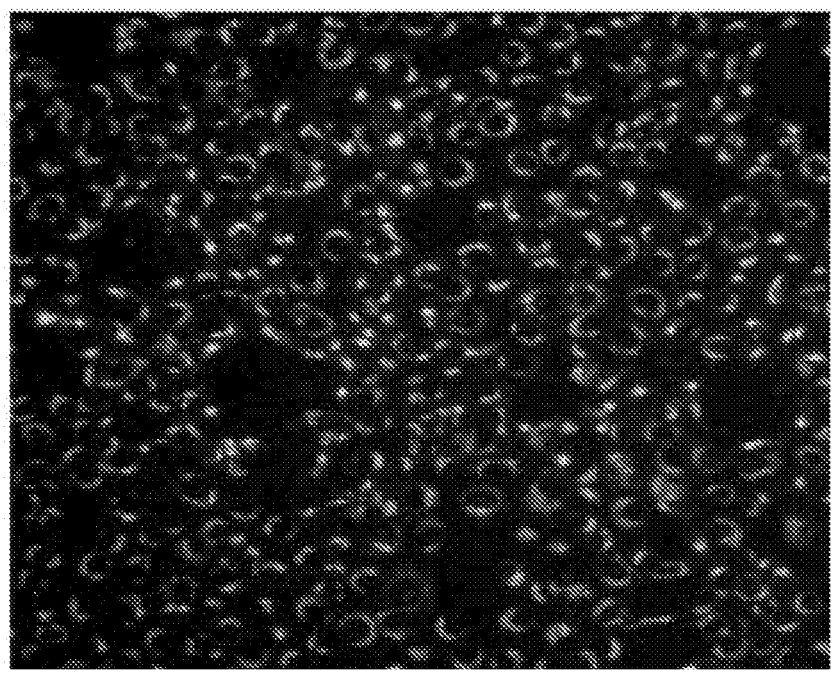
FIGS. 8(A-D) illustrate images and plot showing representative results demonstrating that the rapid replication of SARS CoV in cells (A) is significantly reduced when co-incubated with a SNO (B). Similarly, group data show the rate of virus replication is attenuated (C; closed circle) and cell survival is increased (D) by inclusion of a SNO in the incubation media.
Figure 8B:
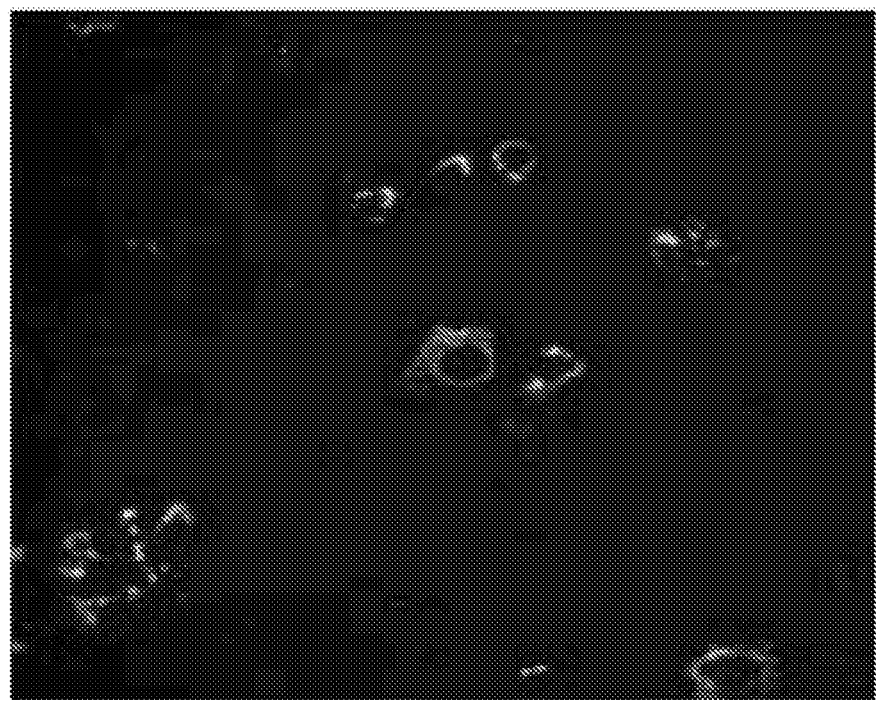
Figure 8C:
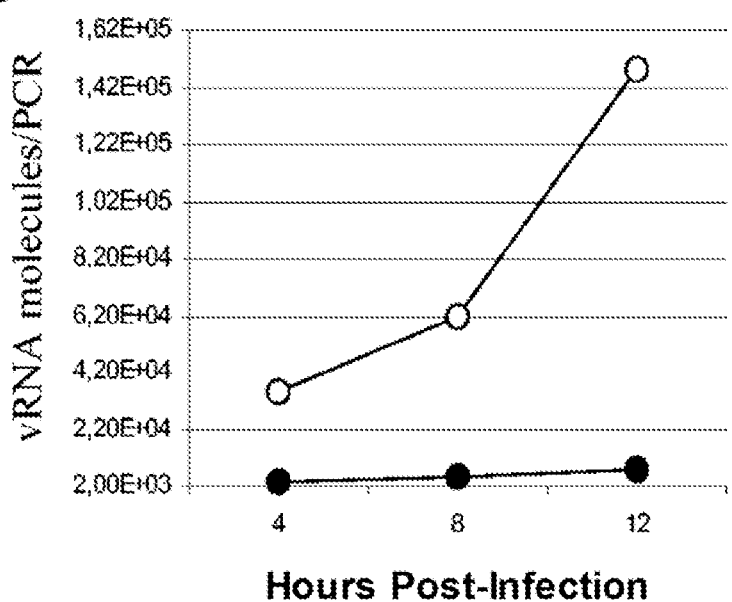
Figure 8D:
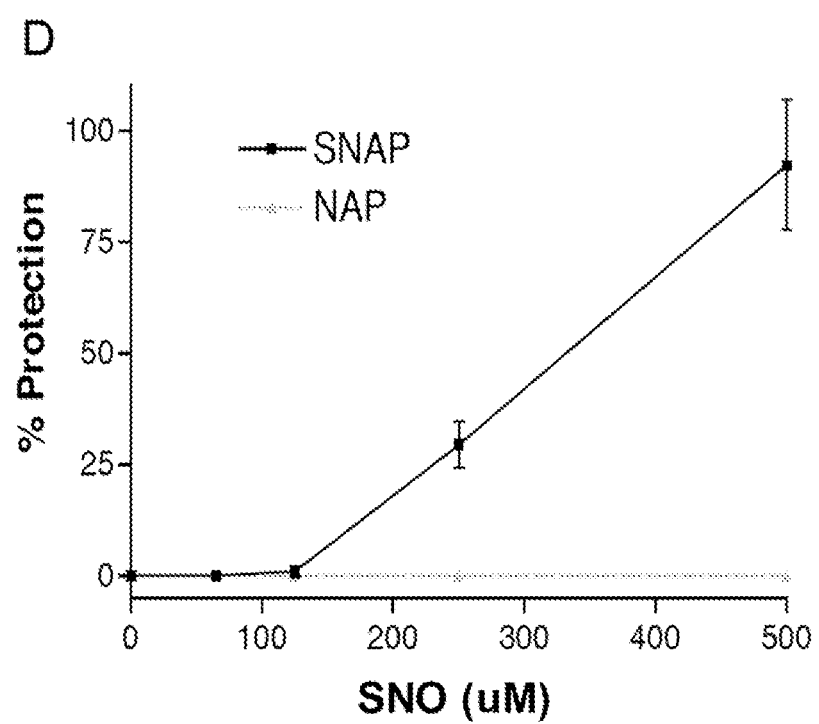

FIGS. 7(A-C) illustrate graphs and a plot showing GSNO has antiviral activity against corona viruses. GSNO significantly reduces infection (Inf; A) and replication (B) of porcine circovirus type 2 (PCV2) (human corona analogue). SNO treatment also significantly reduces viral replication in PCV2-infected mice ((DPI, days post-inoculation; NC, normal control).

FIGS. 8(A-D) illustrate images and plot showing representative results demonstrating that the rapid replication of SARS CoV in cells (A) is significantly reduced when co-incubated with a SNO (B). Similarly, group data show the rate of virus replication is attenuated (C; closed circle) and cell survival is increased (D) by inclusion of a SNO in the incubation media.

Therapies directed toward increasing SNO-Hb and GSNO can restore SNO-regulated control over oxygen exchange and delivery, airway/vascular tone, lung inflammation and lung injury. In addition, SNO restoration may improve host defense and inhibit viral replication. As noted, iNO (inhaled NO) has more limited capabilities to affect these SNO-based parameters as it does not generate GSNO effectively within the lungs or SNO-Hb effectively in blood. As a result, we have focused our attention on the S-nitrosylating agent ENO, a low-molecular-weight (75.07), colorless organic nitrite with a density of 0.9. ENO can be stored as a liquid, but with a low boiling point (16.5 to 17° C.), it is volatile at room temperature, which allows for inhalation or other gaseous routes of delivery. Furthermore, it does not form toxic NOx when mixed with oxygen. More specifically, ENO acts to restore or increase the levels of naturally occurring SNO compounds, i.e., GSNO and SNO-Hb. The breakdown product of these reactions is ethanol in amounts (ppm) that are readily metabolized by the body.

From the above description, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A method of treating a coronavirus infection in a subject in need thereof, the method comprising:
administering to the subject a therapeutically effective amount of ethyl nitrite (ENO), wherein the ENO promotes, increases, and/or induces hemoglobin nitrosylation within red blood cells (RBCs) and GSNO levels in the lung or airways of the subject.

2. The method of claim 1, wherein the coronavirus infection causes respiratory distress in subject.

3. The method of claim 1, wherein the coronavirus infection causes at least one of viral injury, inflammation, peripheral tissue hypoxemia/hemodynamic instability, impaired microvascular blood flow, red blood cell disorder, or a SNO-hemoglobin deficiency like state in the subject.

4. The method of claim 1, wherein the coronavirus infection is a SAR-CoV-2 infection and the coronavirus infection causes COVID-19.

5. The method of claim 1, wherein the ENO produces both GSNO within lungs and SNO-Hb within (RBCs).

6. The method of claim 1, wherein the therapeutically effective amount of ENO is an amount effective to reduce and/or attenuate at least one of viral injury, inflammation, peripheral tissue hypoxemia/hemodynamic instability, blood flow limitation, red blood cell disorder, or an SNO-hemoglobin deficiency like state associated with and/or caused by viral infection of the subject.

7. The method of claim 1, wherein the ENO is in a gaseous form that does not directly release NO.

8. The method of claim 1, wherein the ENO is administered by inhalation, ventilation, or insufflation.

9. The method of claim 1, wherein the ENO is administered in a composition at a concentration of 0.1 to 5,000 ppm.

10. The method of claim 9, wherein the ENO is administered in combination with N-acetyl cysteine.

11. The method of claim 10, wherein ENO is formulated with N-acetyl cysteine for inhalation.

12. The method of claim 10, wherein ENO is formulated with N-acetyl cysteine for intravenous administration.

13. The method of claim 1, wherein the ENO is administered in combination with a GNSOR inhibiting agent, an AKR inhibitor, an N-acetyl cysteine, and/or an anti-viral agent.

14. The method of claim 13, wherein the ENO is administered in combination with a GSNO reductase (GSNOR) inhibiting agent.

15. The method of claim 14, wherein the GSNOR inhibiting agent is selected from the group consisting of an ADH inhibitor, an AKR inhibitor and/or a SNO-CoAR inhibitor.

16. The method of claim 15, wherein the AKR inhibitor is an AKR1A1 inhibitor.

17. The method of claim 15, wherein the GSNOR inhibiting agent is administered to the subject via intraperitoneal administration.

18. The method of claim 13, wherein the therapeutically effective amount of GSNOR inhibiting agent is an amount effective to increase hemoglobin nitrosylation of RBCs and the level of GSNO in the subject's lung tissue.

19. The method of claim 13, the ENO being formulated for inhalation, ventilation, or insufflation, or oral administration.

* * * * *